(12) United States Patent
Gross et al.

(10) Patent No.: US 8,337,869 B2
(45) Date of Patent: Dec. 25, 2012

(54) ANALGESIC CREAM

(76) Inventors: Robert L. Gross, Foster City, CA (US); Nancy L. Leventoff, Foster City, CA (US)

( * ) Notice: Subject to any disclaimer, the term of this patent is extended or adjusted under 35 U.S.C. 154(b) by 760 days.

(21) Appl. No.: 11/834,944

(22) Filed: Aug. 7, 2007

(65) Prior Publication Data

US 2009/0041857 A1 Feb. 12, 2009

(51) Int. Cl.
*A61K 31/74* (2006.01)
*A61K 8/02* (2006.01)
*A61K 33/34* (2006.01)
*A01N 59/20* (2006.01)

(52) U.S. Cl. .................. 424/401; 424/78.03; 424/630

(58) Field of Classification Search .................. None
See application file for complete search history.

(56) References Cited

U.S. PATENT DOCUMENTS

| | | | |
|---|---|---|---|
| 4,464,397 A | 8/1984 | Morelle et al. | |
| 6,217,885 B1 * | 4/2001 | Roder et al. | 424/401 |
| 6,528,076 B2 * | 3/2003 | Small | 424/401 |
| 2002/0176843 A1 * | 11/2002 | Creton | 424/78.37 |
| 2006/0110415 A1 | 5/2006 | Gupta | |
| 2007/0248633 A1 * | 10/2007 | Baldo | 424/401 |

OTHER PUBLICATIONS

Chemidex ASPARLYNE® [Online] retrieved on May 21, 2010 from: http://www.chemidex.com/PersonalCare/Detail/3833/110154; 2 pages.*

Kulkarni, et al. Treatment of osteoarthiritis with a herbomineral formulation: a double-blind, placebo-controlled, cross-over study. Journal of Ethnopharmacology, 33(1-2): 91-95, 1991.

Matteson. Current Treatment Strategies for Rheumatoid Arthritis. Mayo Clinic Proc. 75: 69-74, 2000.

* cited by examiner

*Primary Examiner* — Ernst Arnold

(74) *Attorney, Agent, or Firm* — Seyfarth Shaw LLP; John C. Serio

(57) ABSTRACT

A herbal topical composition is used having complexed trace minerals capable of effectively reducing bone and joint inflammation by inhibiting inflammation pathways and in particular COX-2. The herbal composition having trace elements in a topical carrier reduces inflammation while avoiding the side effects associated with traditional drug therapy.

5 Claims, No Drawings

ANALGESIC CREAM

FIELD OF THE INVENTION

The present invention relates generally to topical herbal compositions having trace minerals for reducing inflammation.

DESCRIPTION OF THE PRIOR ART

Arthritic disorders, including rheumatism, osteoarthritis, dysplasia, lupus, bursitis, and gout, are all characterized by inflammation and pain in bones, joints, muscles, and related connective tissues. Other disorders such as Temporomandibular joint (TMJ) syndrome are also characterized by inflammation and pain. Patients who suffer from inflammation experience pain and discomfort and may lose the effective use of inflamed joints. Prior art methods as to the therapeutic treatment of bone or joint inflammation is the relief of pain and discomfort by the use of anti-inflammatory compounds that may aid in the reduction of the inflammation and pain associated with inflamed joints.

It is well known in the art that certain enzymes play a role in causing inflammation. One of the features of inflammation is increased oxygenation of arachidonic acid, which is metabolized by two enzymatic pathways—the cyclooxygenase (CO) and the 5-lipoxygenase (5-LO) pathways—leading to the production of prostaglandins and leukotrienes, respectively. Prostaglandins and leukotrienes are mediators of inflammation. Therapies that inhibit cyclooxygenase and/or lipoxygenase activity are therefore of great interest in the treatment of inflammation.

Tissue injury and subsequent inflammation represents a complex series of events resulting in the characteristic signs of heat, redness, swelling and pain. Inflammation is characterized by increased vascular permeability and fluid exudation; free radical damage; infiltration by inflammatory cells, neutrophils/phagocytes with release of damaging lysosomal enzymes, cytokines and chemokines; activation of the arachidonic acid cascade with production of pro-infammatory prostaglandin E2 and leukotrienes via the cyclooxygenases (COX-1, COX-2) and lipoxygenase; and mast cell release of biogenic amines (histamine, serotonin); all these processes acting to augment and perpetuate the tissue injury.

There are two forms of the cyclooxygenase enzyme: cyclooxygenase-1 (COX-1) and cyclooxygenase-2 (COX-2). The latter form, i.e., COX-2, appears to play a key role in inflammatory processes. Without being bound to any particular theory, it is thought that inhibiting the COX-2 enzyme may be an effective way to reduce inflammation without the side effects associated with COX-1 inhibition. In addition, recent scientific studies also suggest that COX-2 inhibition may serve an important function in promoting normal cell growth in the colon, pancreas, breast tissue and other organ systems.

The treatment of inflammation has primarily focused on the control/inhibition of the arachidonic cascade. When tissue injury occurs, arachidonic acid is released by the action of phospholipase A2. Arachidonic acid is then acted on by the cyclooxygenase enzymes, COX-1 and COX-2 generating prostaglandin E2 which is pro-inflammatory. Arachidonic acid is also acted on by the enzyme 5-lipoxygenase which generates the pro-inflammatory leukotrienes, in particular leukotriene B4.

The oral non-steroidal compounds (NSAID's) both prescription and non-prescription are the primary treatment approach for inflammatory condition such as arthritis, bursitis, tendonitis, muscle sprains, strains, etc. NSAID's act by inhibiting cyclooxygenase. Recently there has been much concern over the adverse effects of these drugs, in particular the selective COX-2 inhibitors. The systemic inhibition of COX-2 appears to have significant cardiovascular adverse effects.

A therapeutic class of drugs has been developed which are intended to selectively inhibit COX-2 with minimal effect on COX-1. However, despite the emphasis on COX-2 inhibition, these drugs have been recently shown to have serious systemic side effects, e.g., cardiac events, a breakdown in digestive protective mucus, and prevention of normal healing processes. For example, non-steroidal anti-inflammatory drugs (NSAIDS) can have a variety of toxic side effects such as, e.g., gastric erosion and adverse effects on kidneys and liver, and may inadequately regulate the cellular immune functions and secretions of various cytokines.

A major aspect of the mechanism of action of NSAIDS is generally thought to be the inhibition of cyclooxygenase, the enzyme responsible for the biosynthesis of some prostaglandins and certain related autacoids. This inhibition is dependent upon the drug reaching the cyclooxygenase enzyme, indicating that the mode of action is at the level of interaction with the enzyme protein itself. For example, acetaminophen can block the enzyme only in an environment that is low in peroxides, which may explain its poor anti-inflammatory activity since sites of inflammation usually contain high concentrations of peroxides generated by leukocytes. Aspirin acetylates a serine at or near the active site of cyclooxygenase, inhibiting the enzymatic activity. Unfortunately, the most common unwanted side effect of NSAIDS and other aspirin-like drugs is a propensity to induce gastric or intestinal ulceration.

Glucocorticoids have the capacity to prevent or suppress the development of the manifestations of inflammation. Unfortunately, the immunosuppressive and anti-inflammatory actions of the glucocorticoids are inextricably linked because they both result in large part from inhibition of specific functions of leukocytes, in particular, inhibition of lymphokines. Because of their immunosuppressive activity and other related side effects, these compounds are only used in severe and acute cases of inflammation.

One of the main causes of ongoing tissue damage is the generation of highly reactive molecular species called free radicals, such as superoxide and hydroxyl ions. Free radicals cause cellular membrane damage by lipid peroxidation. The main mechanism controlling free radical damage is the scavenging and inactivation of these radicals by the family of enzymes, Superoxide dismutase (SOD). SOD consists of 3 iso-forms based on the trace element that forms the enzyme's active site. The predominant tissue SOD is copper and zinc dependent, i.e. copper-zinc SOD. The other two iso-forms are copper-SOD and manganese-SOD. These SOD iso-forms exist as pro-enzymes until they are activated by the insertion of copper, zinc or manganese into the active site. When activated these enzymes convert the charged, highly reactive superoxide ion into non-reactive hydrogen peroxide.

In the body, when inflammation occurs, copper and zinc are mobilized from the liver and transported to the site of inflammation complexed to amino acids or protein. These organically complexed trace elements then are inserted into the SOD active site, converting the pro-enzyme to a physiologically active, functional enzyme. Control of inflammation depends on the availability of these organically complexed trace elements delivered to the site of inflammation.

Most currently available topical analgesic preparations consist of standard counter-irritant ingredients such as methyl salicylate, menthol, eucalyptus, thymol, etc. in varying combinations and concentrations, with or without such additional ingredients as glucosamine, chondroitin, hyaluronic, emu oil. Other preps use the pepper extract capsaiscin as their primary ingredient. These preps effectively produce temporary symptomatic relief but little else.

Recently the use of natural ingredients, e.g., herbs, have been increasingly used to treat bone and joint inflammation. Although some herbal compositions for reducing inflammation are known, it is desirable to provide alternative herbal compositions capable of reducing inflammation, particularly by inhibiting COX-2, without the unwanted side effects of traditional COX-2 inhibitors.

SUMMARY OF THE INVENTION

It is therefore an object of the present invention to provide a herbal topical composition having trace minerals capable of effectively reducing bone and joint inflammation by inhibiting inflammation pathways and in particular COX-2.

It is a further object to provide an herbal composition having trace elements in a topical carrier capable of reducing inflammation while avoiding the side effects associated with traditional drug therapy.

It is yet another object to provide methods of reducing inflammation using a topical herbal composition having the characteristics set forth in the preceding objects.

It is a further object to provide methods of formulating the topical composition having a herbal composition having the characteristics set forth in the preceding objects.

Other objects and features of the present invention will be apparent from the following detailed description of the preferred embodiment.

It is an object of the present invention to provide compositions that address the various mechanisms of tissue damage caused by inflammation as well as to address more effective injury healing.

It is a further object of the invention to provide compositions that provide symptomatic relief with its counter-irritant ingredient methyl salicylate.

It is yet another object of the invention to provide compositions having copper complexes that reduce inflammation by stabilizing lysosomal membranes in the infiltrating phagocytes, thus limiting the release of tissue damaging enzymes such as proteases.

It is a further object of the invention to provide compositions having copper complexes to stabilize tissue mast cells membranes limiting the release of histamine and serotonin, biogenic amines that increase vascular permeability.

It is another object of the invention to provide a compositions that produce arachidonic acid cascade inhibition locally without systemic effects. Copper is known to directly block the generation of prostaglandin E2 from arachidonic acid.

It is a further object of the invention to provide compositions containing dipotassium glycyrrhizinate (DPG) providing for inhibitory effects on prostaglandin and leukotriene pathways. Production of both PGE2 and LTB4 were inhibited by greater than 50% by concentrations of DPG contained in Theraflex. DPG also has beneficial anti-inflammatory effects by inhibiting release of histamine from mast cells, and by its marked inhibition of hyaluronidase, an enzyme in inflammation that destroys extracellular matrix and connective tissue elements.

It is yet a further object of the invention to provide compositions containing copper complexes to promote healing by providing a component of the enzyme lysyl oxidase. Lysyl oxidase is responsible for the cross-linking and stabilization of both collagen and elastin.

It is another object of the invention to provide compositions containing zinc complexes. Zinc is well-known for its requirement in wound healing, being a key component of many enzymes, including DNA polymerase.

It is also an object of the invention to provide compositions containing asparlyne, the dipeptide lysine-aspartate, providing beneficial muscle effects by decreasing spasm, reducing lactic acid accumulation, increasing efficiency of muscle energy production, and improving recovery time.

It is a further object of the invention to provide a composition that provides immediate symptomatic relief and long term anti-inflammatory and tissue healing effects.

DETAILED DESCRIPTION OF THE INVENTION

Detailed embodiments of the present invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present invention in virtually any appropriately detailed embodiment.

In a first illustrative embodiment, a topical preparation according to the disclosure contains copper pyrrolidone carboxylate (copper PCA), also called copper pyroglutamate. This is contained within a pharmaceutical acceptable topical vehicle at a concentration of about 3.0%. This copper complex is copper bound to an amino acid, pyrrolidone carboxylate (PCA) forming a copper-amino acid chelate. Since PCA is a naturally occurring amino acid in high concentration in the skin, the chelate is exceptionally soluble in water, and it has been shown experimentally to readily pass thru the epidermis of the skin making its penetrability desirable. As the copper in this chelate complex is organically bound, it is immediately usable by the body, as opposed to inorganic copper such as copper sulfate, which has to be organified once in the body. It is contemplated within the scope of the disclosure that other copper-amino acid or copper-protein chelates can be used. Without being bound to any particular theory it is believed that during the inflammatory process, the body mobilizes copper from the liver in the form of copper bound to either amino acid or protein.

Copper is known to play an important role in the body's response to inflammation. Copper accumulates at the site of injury or inflammation and acts to limit its progression and the damage from inflammation. It is thought that copper is key to the activation of superoxide dismutase, the tissue enzyme responsible for inactivating tissue-damaging free radicals (superoxides and hydroxyl). There are three isotypes of superoxide dismuatase (SOD). A primary one is copper dependent. Copper binds to the pro-enzyme making it functional. Copper occupies the active site of the active SOD. Copper has other functions that limit damage in an injury or inflammatory state. It is thought that copper stabilizes the lysosomal membranes in inflammatory cells like neutrophils. This limits the release of damaging lysosomal enzymes (such as proteases) and thus limits further tissue damage. Additionally, copper is known to directly inhibit prostaglandin synthesis, thus limiting the entire cylco-oxygenase pathway and its harmful effects. It is also thought that copper plays an important role in tissue healing. Copper is a required co-factor for the enzyme lysyl oxidase, which is the enzyme that cross-links collagen, strengthening it in the healing process.

In addition to the copper chelate, zinc pyrrolidone carboxylate is optionally present at a concentration of about 0.8%.

This particular zinc chelate is selected for its availability in the body. Organic zinc (bound to protein or amino acid) is how the body delivers zinc to the sites of injury and inflammation. Zinc is required along with copper to activate the primary superoxide dismutase form, copper-zinc-dependent SOD. This primary superoxide is important to the inactivation of damaging free radicals.

It is thought that zinc plays a role in tissue and wound healing. Zinc deficiency is known to be associated with poor tissue healing. Zinc is an essential cofactor for DNA polymerase required for DNA synthesis in any replicating (healing) tissue.

The topical composition according to the disclosure also optionally contains manganese aspartate, a chelate of manganese with the amino acid aspartic acid in a concentration of about 0.04%. This is contained within the topical preparation due to the role of manganese as the essential cofactor for the activation of a third superoxide dismutase isoform, manganese SOD. This is found in the mitochondria, and acts to protect them from free radical damage. This is important to normal cell function, replication/healing, etc., as the mitochondria are the energy producing organelles of the cell.

The topical composition according to the disclosure further optionally contains asparlyne, at a concentration of about 1.0%. Asparlyne is a dipeptide compound consisting of lysine and aspartic acid. This dipeptide has been shown to have beneficial effects on muscle function and recovery. In particular, the accumulation of lactic acid is reduced, thus decreasing muscle stress, improving muscle contractility, and increasing the ability for muscle to recover. Also, reduces muscle fatigue by increasing microcirculation to the muscle. This dipeptide also enhances muscle function by increasing intracellular ATP production, by facilitating glycolysis and enhancing Krebs' cycle activity. Finally, in active muscle, asparlyne acts as a muscle re-polarizer allowing for enhanced muscle recovery time.

The topical preparation according to the disclosure optionally contains methylsulfonylmethane (MSM) at a concentration of about 1.5%. This is an organic sulfur containing molecule which can enhance synthesis of connective tissue and extra-cellular matrix components, including glycosaminoglycans, cartilage, etc. via deliver of its sulfur.

The topical preparation according to the disclosure optionally contains dipotassium glycyrrhizinate (DPG) at a concentration between about 0.5 and about 1.0%. DPG is the purified active ingredient of the extract of licorice, glycyrrhizia glabra. Without being bound to any particular theory it is thought that DPG has multiple anti-inflammatory properties. DPG significantly inhibits the arachidonic acid cascade central to inflammation. It is thought that DPG inhibits prostaglandin E2 production via the cycoloxygenase pathway (COX1,2) in the same method of action as NSAID, such as indomethacin. Additionally, DPG blocks 5-lipoxygenase thus inhibiting the production of leukotrienes another key mediator of inflammation. DPG has been shown to block biogenic amine secretion by tissue mast cells. Specifically it prevents the release of histamine from mast cells, thus preventing the vascular permeability and fluid exudation that occurs during inflammation. Another anti-inflammatory effect of particular benefit is DPG's inhibition of the enzyme hyaluronidase. Hyaluronidase is activated in inflammation and its activity destroys extra-cellular matrix, increases histamine release, and increases blood vessel permeability. DPG's inhibitory effect on hyaluronidase is thought to be greater than that of NSAID, such as indomethacin.

It is also thought that DPG is more effective than both NSAID's and cortisone in preventing post-UV exposure erythema of the skin, a measure of inflammation. It is further thought that DPG enhances the anti-inflammatory effect by inhibiting the metabolism and excretion of endogenous glucocorticoids ("cortisone").

The topical preparation according to the disclosure also optionally contains methyl salicylate-Synthetic oil of wintergreen is used at concentration of about 18-22%. A counterirritant-one of the counterirritants designated by the FDA as required in a topical analgesic.

The topical preparation according to the disclosure optionally also contains aloe vera. at a concentration of about 0.5%.

The topical preparation according to the disclosure optionally also contains Boswellia extract-4:1 extract of boswellia serrata (frankincense). Used at a concentration of about 2.5%. In accordance with the disclosure, a 4:1 extract is prepared by extracting 4 phounds of herb in a gall of alcohol. It is thought that active components of the extract are pentacyclic terpenes of boswellic acid. These components have been shown to be anti-inflammatory due to the inhibition of both 5-lipoxygenase and elastase enzymes.

In a further illustrative embodiment the topical preparation according to the disclosure a topical cream helpful in the treatment of TMJ has all of the ingredients in the first illustrative embodiment listed above, but optionally includes a blend of 6 herbal extracts. This extract blend is a 4:1 extract comprising the following herbs:

Arnica—known to have wound healing properties and used topically for sprains and strains;
Turmeric—anti-inflammatory;
Devil's Claw—anti-inflammatory; used traditionally as a tea for arthritis;
Ginger—anti-inflammatory, wound healing;
Angelica sinensis—used in traditional Chinese medicine specifically for TMJ disorders by direct injection into the TMJ joint;
Smilacis glabra—used in Chinese medicine for painful muscle spasms, joint pain/arthritis, and tendon/ligaments problems; and
White peony—anti-inflammatory, analgesic.

The extract blend is used in the TMJ cream at a concentration of about 7.5%. In addition to the above-mentioned components, other components may be incorporated in the skin preparation of this invention depending on the intended use thereof. Thus, it is possible to prepare skin preparations having a wide variety of rheological properties in a conventional manner. The formulations of these skin preparations include aqueous mixtures such as a solution, colloidal solution, emulsified lotion, O/W cream (hydrophilic cream) and aqueous gel wherein the aqueous phase is the continuous one; oily mixtures such as a solution, ointment, W/O cream, gel base [e.g. Plastibase® (a mineral oil gelled with polyethylene, i.e., a gel of polyethylene and liquid paraffin)], absorption ointment in which an emulsifier is added to the oil and hydrophilic ointment wherein the oil phase is the continuous one; and non-aqueous, water-soluble bases such as a mixture of polyethylene glycol. A suspension base such as a shaking lotion in which a solid dispersing agent is added can also be prepared.

Oily components, emulsifiers, dispersing agents, gelatinizers and solid materials which can be used to prepare such formulations are well known as those used in the preparation of cosmetics and topical products.

The oily components include hydrocarbons such as liquid paraffin, vaseline, solid paraffin, microcrystalline wax, etc.; higher aliphatic alcohols such as cetyl alcohol, hexadecyl alcohol, stearyl alcohol, oleyl alcohol, etc.; esters of higher fatty acids with higher alcohols such as beeswax, spermaceti, etc.; esters or higher fatty acids with lower alcohols such as isopropyl myristate, isopropyl palmitate, etc.; vegetable oils, modified vegetable oils, hydrous lanolin and its derivative, squalene, squalane; higher fatty acids such as palmitic acid, stearic acid, etc. and the like. In one illustrative embodiment according to the disclosure, sweet almond oil is used at concentration of about 1.0%. The almond oil is added to the topical preparation according to the disclosure for its texture and emollient function. Its fatty acid profile substantially reflects that present in the skin protective layers. Additionally capric/capryllic triglycerides are added at a concentration of about 1.0%.

Emulsifiers and dispersing agents which can be used include anionic, cationic and nonionic surfactants. Nonionic surfactants are preferred because of their low levels of irritation to skin. Typical of nonionic surfactants are fatty acid monoglycerides such as glyceryl monostearate, etc.; sorbitan fatty acid esters such as sorbitan monolaurate; etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc. In one illustrative embodiment according to the disclosure, glyceryl stearate, in a concentration of about 2.0% is used as an emulsifier in combination with a further emulsifier Tween—polysorbate at concentration of about 0.3% and Arlacel-165®, which is a combination of glyceryl stearate and PEG-100 stearate (polyethylene glycol-100 units bound to stearate in a concentration of about 2.0%

Particularly in the preparation of creams according to the invention, the use of a polyoxyethylene fatty acid ester is advantageous in that the emulsion stability is highly improved. Particularly preferred for this purpose are those polyoxyethylene fatty acid esters wherein the fatty acid contains usually about 8 to 26 carbon atoms, preferably about 12 to 18 carbon atoms and the number of ethylene oxide molecules in the addition polymerized polymer chains (or degree of addition polymerization of ethylene oxide) is usually about 20 to 60, preferably about 40 to 55. An example of such ester is polyoxyethylene monostearate. In one illustrative embodiment according to the disclosure, Polawax an emulsifying wax is used at concentration of about 5.0%.

Gelatinizers include but are not limited to carboxymethylcellulose, cellulose gel, carbopol, polyvinyl alcohol, polyethylene glycol and various gums.

These oily components, emulsifiers, dispersing agents and gelatinizers, of course, can be used alone or in combination with each other.

The incorporation into the skin preparation of this invention of propylene glycol, glycerine, sorbitol or the like which has a moisturizing action is preferred, because it enhances the moisturizing action of the skin preparation of this invention. Ethanol may be added to advantage, since it has a bacteriostatic action and provides a cooling effect upon application to the skin.

In order to further increase the stability of the skin preparation of this invention it is preferred to add a chelating agent, an antiseptics, a perservative and the like, as required. The chelating agents which can be used include EDTA (ethylenediamine tetracetate), thioglycolic acid, thiolactic acid, thioglycerine and the like. The antiseptics which can be used include methyl, ethyl, propyl and butyl esters of p-hydroxybenzoic acid, o-phenylphenol, dehydroacetic acid and the salts thereof, p-chloro-m-cresol, p-chloro-m-xylenol and the like. In one illustrative embodiment according to the disclosure, butylated hydroxytoluene (BHT) is used at a concentration of about 0.15% as a preservative.

In addition, it is preferred to adjust pH of the skin preparation by adding citric acid, lactic acid, tartaric acid or the like. The pH value which should be adjusted to is dependent upon the stability of the skin preparation. In general, it is preferred that the skin preparation be slightly acidic to slightly alkaline. A fragrance and or pigment may be added in a slight amount, if desired to improve the merchantability of the topical preparation.

In addition, the skin preparations of this invention disperse and retain the active ingredients in the skin for a prolonged period of time without loss of activity so that they can exert the effect of the ingredients effectively.

The following examples are given to illustrate this invention, but they are not intended to restrict the invention in any way.

Example I

In accordance with the invention, an analgesic cream in a first illustrative embodiment is comprised of four distinct parts that are as follows:

| Part A | |
|---|---|
| Distilled, Deionized Water | 52.45% |
| Copper Pyrollidone Carboxylate (PCA) | 3.0% |
| Zinc Pyrrolidone Carboxylate (PCA) | 1.0% |
| Methyl Sulfonyl Methane (MSM) | 1.5% |
| *Aloe Vera* | 1.0% |
| Tween 80 (polysorbate) | 0.6% |
| Manganese Aspartate | 0.04% |
| Part B | |
| Asparlyne (Lysine Aspartate) | 1.0% |
| Part C | |
| 4:1 extracts of the following herbs: | |
| *Arnica* 5 parts | 7.5% |
| *Angelica sinensis* 4.5 parts | |
| White Peony 2.5 parts | |
| Frankincense (Boswella) 2.5 parts | |
| Devil's Claw 1.5 parts | |
| Turmeric 1.0 parts | |
| Smilacis 1.0 parts | |
| Part D | |
| Polawax | 5.0% |
| Arlacel 165 | 2.0% |
| Glyceryl Stearate | 2.0% |
| Methyl Salicylate | 18.0% |
| Capric/Capryllic Triglycerides | 1.0% |
| Meadow Foam Oil | 1.5% |
| Butylated Hydroxytoluiene (BHT) | 0.15% |
| Germaben II | 2.0% |

Example II

| 1. Distilled, de-ionized water | 58.2% |
|---|---|
| Group A | |
| 2. Copper PCA | 3.0% |
| 3. Zinc PCA | 0.8% |
| 4. Manganese aspartate | 0.04% |
| 5. MSM | 1.5% |
| 6. Tween | 0.3% |
| 7. *Aloe Vera* | 0.5% |
| 8. *Boswellia* extract | 2.5% |

-continued

Dissolve ingredients in Group A in water and heat to 70 degrees C.

Group B

| 9. Methyl salicylate | 20.0% |
| 10. Polawax | 5.0% |
| 11. Arlacel 165 | 2.0.% |
| 12. Glyceryl stearate | 2.0% |
| 13. Capric/capryllic TG's | 1.0% |
| 14. Sweet almond oil | 1.0% |
| 15. BHT | 0.2% |

Heat ingredients in Group B to 70 degrees C.

Group C

| 16. Asparlyne | 1.0% |
| 17. Dipotassium glycyrrhizinate | 1.0% |

Dissolve DPG in water at room temp. Add to Asparlyne.

Add Group A to Group B with both at 70 degrees C. to form an emulsion. Stir constantly. At 40 degrees C add Group C and continue mixing and cooling until stable cream is formed.

Although the illustrative embodiments show the topical analgesic cream without non-steroidal anti-inflammatory compounds, it will be appreciated by those skilled in the art that the topical analgesic cream according to the disclosure can have one or more non-steroidal anti-inflammatory compounds incorporated into the composition. Likewise, it will be understood that other pharmaceutically active compounds such as corticosteroids can be incorporated alone or in combination in the topical analgesic cream according to the invention.

It will be understood that various modifications may be made to the embodiments and examples disclosed herein. Therefore, the above description and examples should not be construed as limiting, but merely as exemplification of the various embodiments. Those skilled in the art will envision other modifications within the scope and spirit of the claims appended hereto.

What is claimed is:

1. A topical composition having anti-inflammatory properties consisting of:
   at least one complexed trace mineral consisting of copper organically bound to pyrrolidone carboxylate forming a copper-amino acid chelate;
   about 0.5 to about 1.0% dipotassium glycyrrhizinate;
   at least one herbal extract;
   about 10 to about 30% methyl salicylate; a component selected from the group consisting of methylsulfonylmethane, at least one non-steroidal anti-inflammatory alone or in combination, lysine-aspartate, at least one steroidal anti-inflammatory alone or in combination, and at least on non-steroidal anti-inflammatory and at least one non-steroidal anti-inflammatory and
   a pharmaceutically acceptable carrier composition.

2. The topical composition according to claim 1, wherein at least one herbal extract is selected from the group consisting of boswellia serrata, aloe vera, arnica, White peony, Turmeric, Devil's Claw, Ginger, angelica sinensis and smilacis glabra.

3. The topical composition according to claim 1 wherein said pharmaceutically acceptable carrier composition is selected from the group consisting of gel, cream and ointment.

4. A method of treating inflammation comprising:
   applying a topical preparation of claim 1 to a subject in need thereof.

5. The method of treating inflammation according to claim 3 wherein at least one herbal extract is selected from the group consisting of boswellia serrata, dipotassium glycyrrhizinate, aloe vera, arnica, White peony, Turmeric, Devil's Claw, Ginger angelica sinensis and smilacis glabra.

* * * * *